(12) United States Patent
Peesay

(10) Patent No.: US 6,526,966 B1
(45) Date of Patent: Mar. 4, 2003

(54) SUCKLING NEBULIZER

(76) Inventor: Marorji R. Peesay, 88 Windingwood Dr., Apt. 4A, Sayreville, NJ (US) 08872

(\*) Notice: Subject to any disclaimer, the term of this patent is extended or adjusted under 35 U.S.C. 154(b) by 0 days.

(21) Appl. No.: 09/500,836

(22) Filed: Feb. 10, 2000

(51) Int. Cl.$^7$ ............................................. A61M 11/00
(52) U.S. Cl. ........................ 128/200.21; 128/200.14; 128/203.12; 128/203.29; 215/11.1
(58) Field of Search ............ 128/200.14, 200.21–200.24, 128/203.12, 203.24, 203.25, 203.28, 203.29, 204.28; 215/11.1, 6

(56) References Cited

U.S. PATENT DOCUMENTS

| | | | |
|---|---|---|---|
| 1,366,437 A | | 1/1921 | Wagenhorst |
| 2,023,267 A | | 12/1935 | De Saint Rapt et al. |
| 2,709,434 A | \* | 5/1955 | Pancoast .................... 215/11.1 |
| 2,812,764 A | \* | 11/1957 | Crisp ........................ 215/11.1 |
| 3,067,425 A | | 12/1962 | Colley |
| 3,145,867 A | \* | 8/1964 | Roberts et al. ............. 215/11.1 |
| 3,359,568 A | | 12/1967 | Kothe |
| 3,426,755 A | \* | 2/1969 | Clegg .................... 128/203.12 |
| 4,475,559 A | \* | 10/1984 | Horn ..................... 128/207.18 |
| 4,520,809 A | \* | 6/1985 | DeGreef et al. ....... 128/200.24 |
| 4,580,556 A | | 4/1986 | Kondur |
| 4,629,080 A | \* | 12/1986 | Carveth ...................... 215/11 |
| 4,657,151 A | \* | 4/1987 | Cabernoch .................. 215/11 |
| 4,669,461 A | | 6/1987 | Battaglia et al. |
| 4,676,387 A | \* | 6/1987 | Stephenson et al. ......... 215/11 |
| 4,711,359 A | \* | 12/1987 | White et al. ............... 215/11.1 |
| 4,809,692 A | \* | 3/1989 | Nowacki et al. ....... 128/206.24 |
| 4,821,895 A | \* | 4/1989 | Roskilly .................... 215/11.1 |
| 4,832,015 A | \* | 5/1989 | Nowacki et al. ....... 128/205.23 |
| 4,886,055 A | \* | 12/1989 | Hoppough ............. 128/200.14 |
| 4,890,609 A | | 1/1990 | Wilson, II |
| 4,896,666 A | | 1/1990 | Hinkle |
| 4,938,209 A | \* | 7/1990 | Fry ....................... 128/200.21 |
| 5,060,811 A | \* | 10/1991 | Fox ................................ 215/6 |
| 5,129,532 A | \* | 7/1992 | Martin ...................... 215/11.1 |
| 5,190,174 A | \* | 3/1993 | Klag ......................... 215/11.1 |
| D343,701 S | \* | 1/1994 | Dahlstrand .................... D29/7 |
| 5,301,825 A | \* | 4/1994 | DiScala et al. ............ 215/11.1 |
| 5,357,945 A | \* | 10/1994 | Messina ................. 128/200.14 |
| 5,375,593 A | \* | 12/1994 | Press ..................... 128/207.18 |
| 5,383,906 A | \* | 1/1995 | Burchett et al. ............. 606/236 |
| 5,411,155 A | \* | 5/1995 | Gordon et al. ............. 215/11.1 |
| 5,462,050 A | | 10/1995 | Dahlstrand |
| 5,586,551 A | \* | 12/1996 | Hilliard ................. 128/203.29 |
| 5,593,052 A | \* | 1/1997 | McGee ....................... 215/11.1 |
| 5,611,776 A | \* | 3/1997 | Simmons et al. ............. 604/65 |
| 5,664,705 A | \* | 9/1997 | Stolper ........................ 222/212 |
| 5,685,291 A | \* | 11/1997 | Marsh .................... 128/200.15 |
| 5,758,786 A | \* | 6/1998 | John .............................. 215/6 |
| 5,810,003 A | \* | 9/1998 | Findlater ............... 128/203.12 |
| 5,853,002 A | \* | 12/1998 | Kawasaki ............... 128/200.14 |
| 5,868,131 A | \* | 2/1999 | Murchie ................. 128/204.13 |
| 5,904,140 A | \* | 5/1999 | McGoogan ............ 128/200.24 |
| 6,042,850 A | \* | 3/2000 | Ida et al. ........................ 426/2 |
| 6,053,342 A | \* | 4/2000 | Chomik ..................... 215/11.5 |
| 6,073,788 A | \* | 6/2000 | Stroud ........................ 215/11.1 |
| 6,076,520 A | \* | 6/2000 | Cooper .................. 128/200.21 |
| 6,092,680 A | \* | 7/2000 | Pillado ...................... 215/11.1 |
| 6,158,428 A | \* | 12/2000 | Mecikalski ............. 128/200.23 |
| 6,173,850 B1 | \* | 1/2001 | Scheetz, Jr. et al. ....... 215/11.1 |
| 6,253,936 B1 | \* | 7/2001 | Kong ........................ 215/11.3 |
| 6,305,562 B1 | \* | 10/2001 | Chan et al. ................ 215/11.1 |

\* cited by examiner

*Primary Examiner*—Dennis Ruhl
*Assistant Examiner*—Joseph F Weiss, Jr.
(74) *Attorney, Agent, or Firm*—Woodcock Washburn LLP

(57) ABSTRACT

The present invention is a nebulizer for infants which provides a respirable gas to an infant while the infant is suckling. The respirable gas may be oxygen or a respirable gas containing a medication. In a first series of embodiments, a feeding bottle is provided so that the infant may bottle feed. In a second preferred embodiment, a pacifier is provided so that the infant may suckle while the respirable gas is administered.

1 Claim, 3 Drawing Sheets

SUCKLING NEBULIZER

FIELD OF THE INVENTION

The present invention relates generally to a nebulizer, and more particularly to a nebulizer having a nipple, such as found in a pacifier or feeding bottle, for suckling infants.

BACKGROUND OF THE INVENTION

Delivery of a respirable gas to a newborn infant and toddler can pose difficulties, especially during times of illness. In addition, infants of ten need supplemental oxygen during periods of activity such as feeding. Oxygen consumption is known to increase during feeding, and infants with low oxygen saturation often cannot feed adequately.

Thus, it is desirable to supplement the infant's oxygen level to ensure proper feeding. Since infants tend to breathe through the nose until three to six months of age, a smooth, constant flow of respirable gas, directed in front of the infant's nose, is a preferred way to administer a respirable gas. However, providing a source of supplemental oxygen as well as food has here before been considered to be a difficult task for a single individual. Nonetheless, the ability to hold and feed a baby is an important need and an integral part of the parent-child bonding process.

Further, the problem that infants are highly distressed by the use of ordinary nebulizers and that a much felt need to calm and sooth an infant during the use of the nebulizer has been long sought in order to have an efficacious administration of a respiratory gas. This problem is addressed and solved by the invention, particularly with the novel and unique use of the pacifier and/or feeding nipple according to the present invention.

Accordingly, the present invention addresses the above-mentioned concerns, as well as others, with a device that provides a simple, safe, and effective means for delivering a respirable gas to an infant at all times, including at times of feeding.

SUMMARY OF THE INVENTION

The present invention is a nebulizer for infants which provides a respirable gas to an infant while the infant is suckling. The respirable gas may be oxygen or a respirable gas containing a medication. In a first series of embodiments, a feeding bottle is provided so that the infant may bottle feed. In a second preferred embodiment, a pacifier is provided so that the infant may suckle while the respirable gas is administered.

Each of the embodiments include a nebulizer, preferably a nebulizer designed according to the present invention, for providing respirable gas. The outlet of the nebulizer is attached to a gas delivery guide, where the gas delivery guide directs the flow of the respirable gas to the nose of the suckling infant. The gas delivery guide includes a generally cylindrical sleeve for receiving and retaining the nebulizer. The cylindrical sleeve further permits gas flow from the nebulizer into the main portion of the gas delivery guide. A generally curved surface of the gas delivery guide directs the respirable gas to the nose of the infant.

A feeding bottle is attached to the gas delivery guide to permit the infant to bottle nurse while being nebulized. A first preferred embodiment of the feeding bottle includes a partition that divides the interior of the feeding bottle into two separate chambers. The partition is preferably inclined to encourage air introduced during nursing to reside away from the nipple area. Further, the neck and/or nipple of the feeding bottle is oriented at an angle to further encourage the air to reside away from the nipple area. A second preferred embodiment of the feeding bottle includes a collapsible bladder that collapses as the liquid is consumed and thus limits the introduction of air into the bladder.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
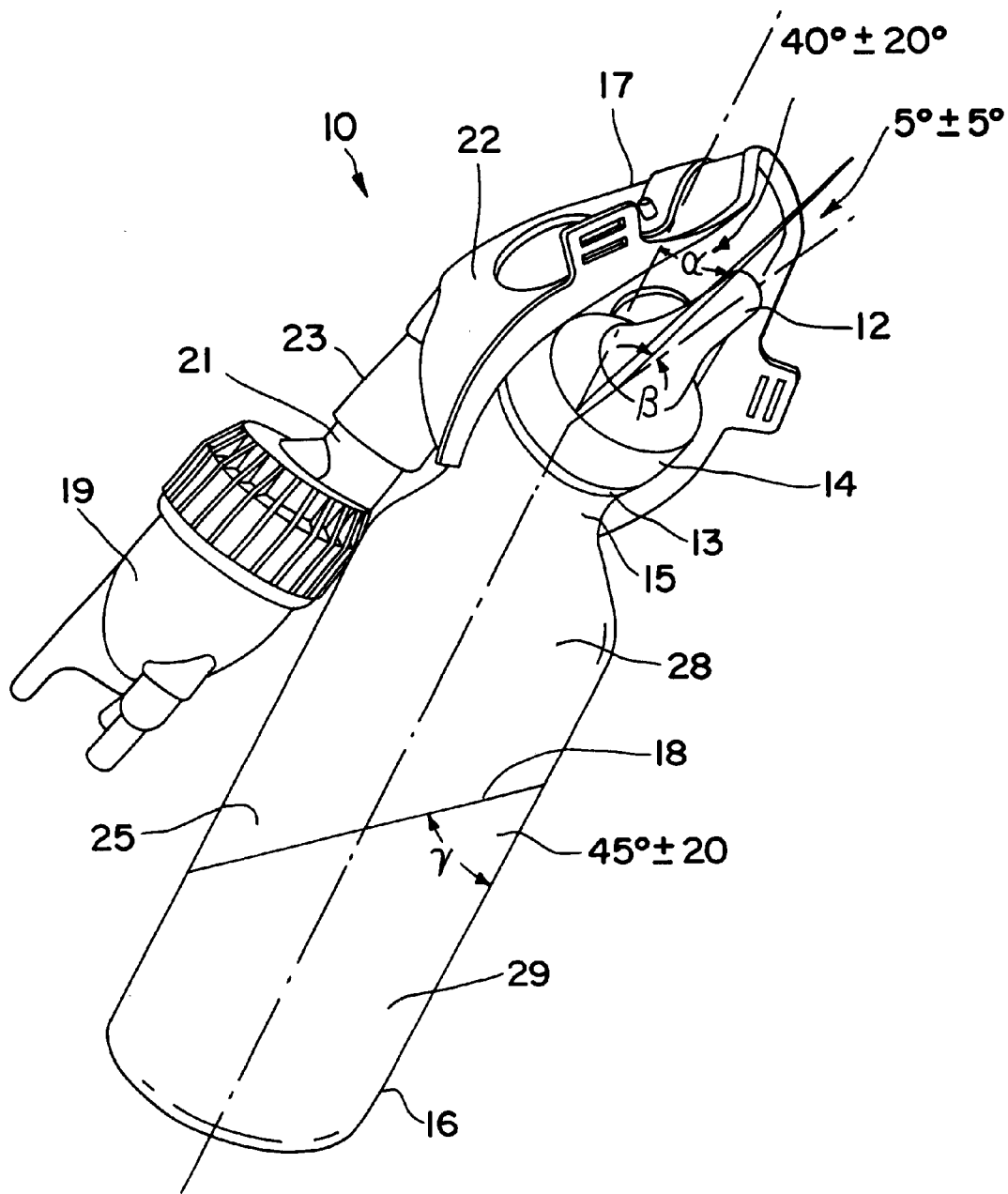
FIG. 1 illustrates a perspective view of a first preferred embodiment of the suckling nebulizer of the present invention having a feeding bottle.

Referring now to the drawings, wherein like numerals indicate like elements, there is shown in FIG. 1 an illustration of a first preferred embodiment of the present invention for both feeding and nebulizing an infant. Suckling nebulizer 10 includes a nebulizer 19, a gas delivery guide 22, and a feeding bottle 16. The nebulizer 19 provides a source of respirable gas, such as oxygen or a medicated gas. The nebulizer 19 maybe a standard nebulizer which is sufficiently compact and lightweight to facilitate ease of handling of the suckling nebulizer 10. A cylindrical neck 21 of the nebulizer 19 connects an outlet (not shown) of the nebulizer 19 to a cylindrical sleeve 23 of the gas delivery guide 22. The cylindrical sleeve 23 has an internal diameter sized to receive the cylindrical neck 21 and preferably forms a gas-sealed connection between the cylindrical sleeve 23 and the cylindrical neck 21. The cylindrical sleeve 23 is open to the interior of the gas delivery guide 22 and permits gas flow between the nebulizer 19 and the gas delivery guide 22. The nebulizer 19 may be held within the cylindrical sleeve 23 by methods commonly known in the art. For example, the cylindrical sleeve 23 may contain threads on its interior surface which mate with complementary threads on the exterior of the cylindrical neck 21. Alternatively, the cylindrical sleeve 23 and the cylindrical neck 21 may attach via a bayonet style mount.

The gas delivery guide 22 is formed to receive the gas flow from the nebulizer 19 through the cylindrical sleeve 23, and includes a curved upper surface 17 to direct the flow of gas toward the nose of a suckling infant (not shown). The gas delivery guide 22 is attachable to the feeding bottle 16. Preferably, the delivery guide 22 attaches to the feeding bottle 16 at the neck 15 of feeding bottle 16. The delivery guide 22 is designed to orient specially designed feeding bottle 16 and the gas delivery guide 17 so that an infant is correctly positioned to simultaneously breath the respirable gas and feed from the bottle 16.

The specially designed feeding bottle 16 of the first preferred embodiment includes a hollow interior which is divided into a first chamber 28, and a second chamber 29 by a partition 18. The partition 18 prevents fluid communication between the first and second chambers 28, 29. The first chamber 28 is designed to hold a liquid for feeding to an infant and is in fluid communication with a nipple 12 which is attached to the feeding bottle 16 by a cap 14. The cap 14 attaches to the neck 15 of the feeding bottle 16 by any suitable method. The angle of tilt of the nipple 12, the neck 15, and the partition 18 are selected to minimize the possibility of ingestion of air by a feeding infant.

As an infant feeds and liquid is removed from the first chamber 28, air is introduced into the first chamber 28 to replace the consumed liquid. The relative dispositions of the nipple 12, neck 15, and partition 18 are designed to keep this air away from the nipple 12. Specifically, the partition 18 is tilted with respect to a longitudinal axis of the feeding bottle 16, such that the edge of the partition 18 closest to the nebulizer 19 is positioned furthest away from the nipple 12. As a consequence of this tilting, the edge of the partition 18 farthest away from the nebulizer 19 is closest to the nipple 12. Preferably, the angle of tilt γ(gamma) is between 0 degrees and 90 degrees. Preferably, the angle of tilt is about 45 (+/−20) degrees. This creates an air capture region 25 into which the introduced air may reside. To encourage the introduced air to rise and reside in the air capture region 25, the neck 15 of the feeding bottle 16 is inclined with respect to the longitudinal axis of the feeding bottle 16. Preferably the neck 15 is tilted in a direction to orient the sidewall 13 of the neck 15 to be more parallel to the plane of the partition 18. More preferably, the neck 15 is tilted at an angle, α (alpha) of 0 degrees to 90 degrees. Most preferably the neck 15 is tilted at an angle of 40 (+/−20) degrees. In addition, the nipple 12 may be tilted in the same direction as the neck 15. The nipple 12 is tilted at an angle, β (beta), of 0 degrees to 10 degrees, and preferably at an angle of 5 (+/−5) degrees.

Figure 2:
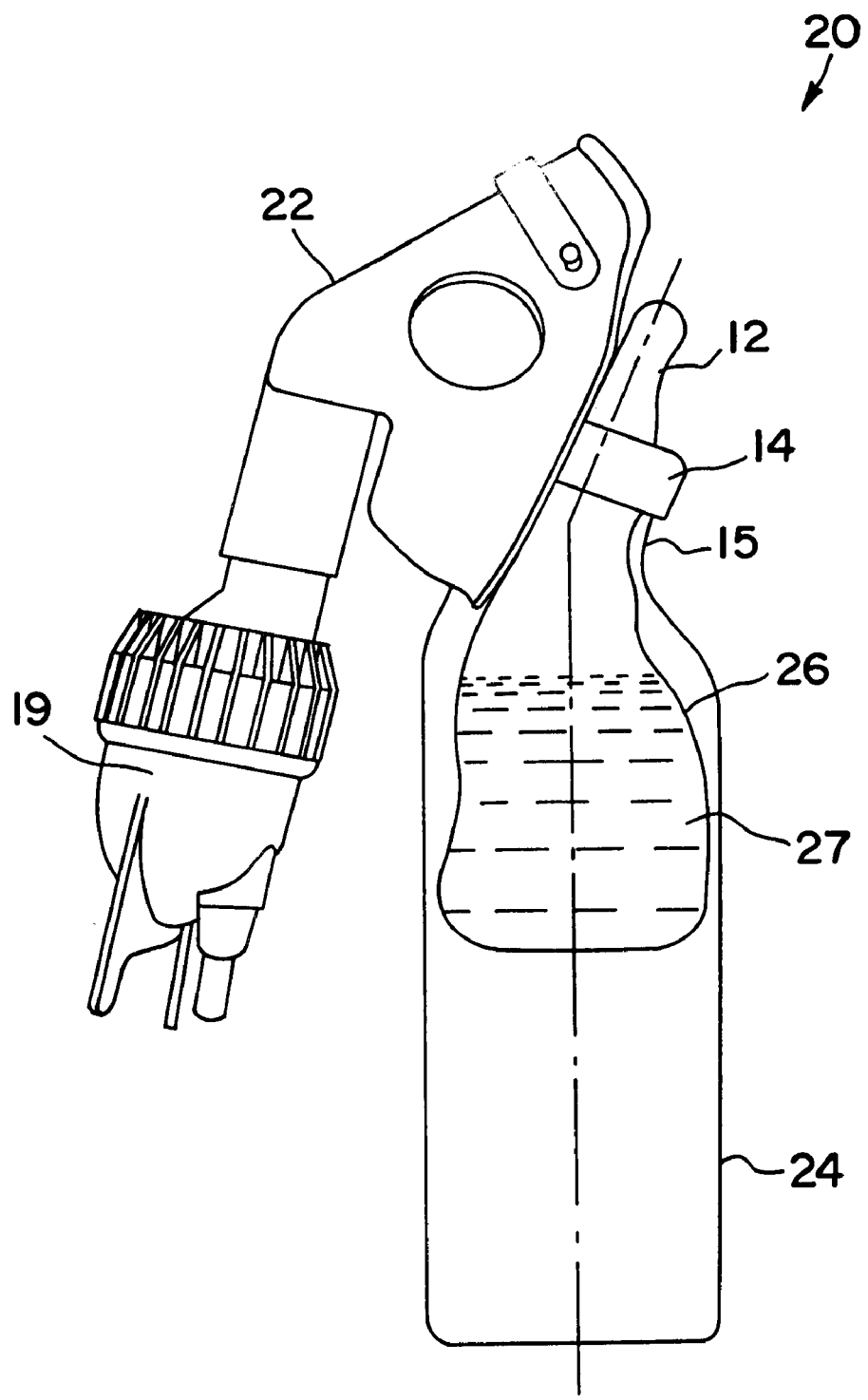
FIG. 2 illustrates a side elevational view of a second preferred embodiment of the suckling nebulizer of the present invention having a feeding bottle.

A second embodiment 20, for both feeding and nebulizing an infant, is shown in FIG. 2. This second preferred embodiment is similiar to the first preferred embodiment of FIG. 1 with the exception of a feeding bottle 24. Specifically, feeding bottle 24 does not include a partition 18 but rather includes a collapsible bladder 26. The collapsible bladder 26 is in fluid communication with the nipple 12, and is capable of holding a liquid 27 for feeding to an infant. As liquid is removed from the collapsible bladder 26, the collapsible bladder 26 collapses inhibiting the introduction of air into the collapsible bladder 26. The nipple 12 and the neck 15 are oriented with respect to the feeding bottle 24 in analogous manner as they are with respect to the feeding bottle 16. In an alternate embodiment, the feeding bottle 24 includes a collapsible bladder where the nipple 12 and neck 15 are tilted with respect to the longitudinal axis of the feeding bottle, the neck or the nipple 12.

Figure 3:
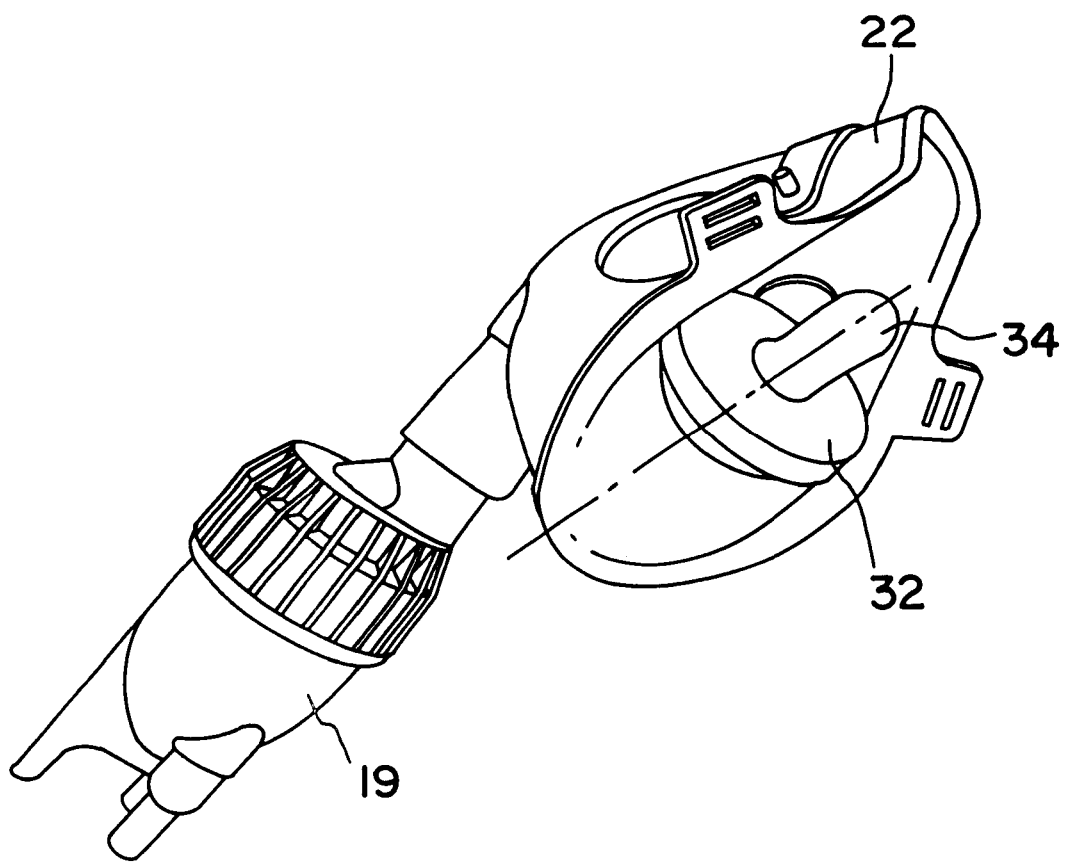
FIG. 3 illustrates a perspective view of a third preferred embodiment of the suckling nebulizer of the present invention having a pacifier.

A third preferred embodiment for nebulizing an infant is shown in FIG. 3 in which a pacifier 32 replaces the feeding bottle 16. The nebulizer 19 and gas delivery guide 22 may substantially identical to these shown in FIGS. 1 and 2. In place of the feeding bottle 16, a pacifier 32 provides a nipple 34 for suckling an infant. As the infant suckles on the pacifier 32, a respirable gas provided by the nebulizer 19 is directed to the nose of the infant by the gas delivery guide 22.

These and other advantages of the present invention will be apparent to those skilled in the art from the foregoing specification. Accordingly, it will be recognized by those skilled in the art that changes or modifications may be to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A nebulizing apparatus for an infant, comprising:

a nebulizer;

a gas delivery guide in communication with the nebulizer; and a feeding bottle connected to the gas delivery guide or nebulizer to calm the infant by allowing the infant to feed during use of the nebulizer, the feeding bottle including:

a neck, the neck angularly disposed with respect to a longitudinal axis of the feeding bottle by about 20 degrees to about 60 degrees;

a cap in communication with the neck;

a nipple in communication with the cap, the nipple angularly disposed with respect to an axis perpendicular to a surface of the cap by about 0 degrees to about 5 degrees; and a chamber for holding liquid food, the chamber including a partition dividing the chamber into a first sub-chamber and a second sub-chamber, the partition preventing fluid communication between the first sub-chamber and the second sub-chamber, the partition being angularly disposed with respect to the longitudinal axis of the feeding bottle by about 25 degrees to about 65 degrees, the partition being substantially parallel to a longitudinal axis of the nipple, the angularly disposed partition defining an air capture region in the first sub-chamber, whereby the air capture region and the parallel relationship of the partition and the longitudinal axis of the nipple encouraging air introduced into the first sub-chamber during infant feeding to reside in the air capture region to minimize a possibility of air ingestion by the infant during feeding.

* * * * *